United States Patent [19]

Remy

[11] 3,957,871

[45] May 18, 1976

[54] CHEMICAL COMPOUNDS AND THE PROCESS FOR PREPARING SAME

[75] Inventor: David C. Remy, North Wales, Pa.

[73] Assignee: Merck & Co., Inc., Rahway, N.J.

[22] Filed: Feb. 7, 1975

[21] Appl. No.: 548,121

Related U.S. Application Data

[60] Division of Ser. No. 216,264, Jan. 7, 1972, Pat. No. 3,882,130, which is a continuation-in-part of Ser. No. 861,987, Sept. 29, 1969, Pat. No. 3,719,712.

[52] U.S. Cl. ..................... 260/562 R; 260/649 R; 260/562 P
[51] Int. Cl.² ........................................ C07C 103/34
[58] Field of Search .......... 260/562 R, 562 P, 649 R

[56] References Cited
UNITED STATES PATENTS

| | | | |
|---|---|---|---|
| 3,118,941 | 1/1964 | Swett et al. .................. | 260/510.5 |
| 3,555,071 | 1/1971 | Reo et al. ..................... | 260/562 P |
| 3,673,190 | 6/1972 | Seiber et al. .................. | 260/649 R |
| 3,751,446 | 8/1973 | Heck ............................ | 260/649 R |

*Primary Examiner*—C. Davis
*Attorney, Agent, or Firm*—Daniel T. Szura; Harry E. Westlake, Jr.

[57] ABSTRACT

This application discloses methods of preparing styrylaralkylamines and phenylethynylaralkylamines. The reaction of an N-formyl iodo benzylamine with a metal phenylacetylide followed by reduction or hydrolysis produces the desired phenylethynyl benzylamine. The corresponding styrylaralkylamine is produced by a catalytic hydrogenation of the phenylethynyl benzylamine.

5 Claims, No Drawings

CHEMICAL COMPOUNDS AND THE PROCESS FOR PREPARING SAME

This is a division of application Ser. No. 216,264, filed Jan. 7, 1972, now U.S. Pat. No. 3,882,130, which in turn is a continuation-in-part of Ser. No. 861,987 filed Sept. 29, 1969 now U.S. Pat. No. 3,719,712, issued Mar. 6, 1973.

This invention relates to unsaturated derivatives of aralkylamine compounds. More specifically, it relates to substituted and unsubstituted derivatives of styrylaralkylamines, phenylethynyl aralkylamines and the corresponding N-substituted derivatives such as the n-alkyl and N,N-dialkyl derivatives thereof.

This invention also relates to the novel processes and the novel intermediates utilized in the production of new aralkylamines, to pharmaceutical formulations of the new aralkylamines and to methods of treating or preventing cardiac arrhythmias using the novel compounds and/or pharmaceutical formulations thereof, described hereinafter.

The new compounds of our invention are 1,2-diaryl derivatives of ethylene or acetylene wherein one of the aryl substituents is an aromatic ring having at least one of its hydrogens replaced by a stright or branched chain amino alkyl radical, or an amino heterocyclic radical, and in which the other substituent is a homocyclic or heterocyclic ring selected from aryl, substituted aryl, heterocyclic and substituted heterocyclic substituents. The compounds of my invention are represented structurally as follows:

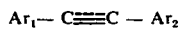

in which $Ar_1$ is a substituted or unsubstituted phenylalkylamine substituent and $Ar_2$ is a substituted or unsubstituted aromatic ring.

A preferred class of compounds of our invention are represented structurally as aralkylamines of the formula:

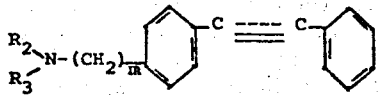

in which $m$ is an integer varying from 1 to 4 inclusive and in which one or more of the methylene ($CH_2$) hydrogens may be replaced by a lower alkyl substituent. $R_2$ and $R_3$ are either similar or dissimilar and are either hydrogen, alkyl (preferably of from 1 to 6 carbon atoms), branched chain alkyl, alkenyl, alkynyl (each preferably containing 1 to 6 carbon atoms), and can be joined together or alternatively may be linked through an atom of carbon, nitrogen, oxygen, or sulfur to one of the methylene substituents of the alkylene side chain to form a heterocyclic ring of 1-morpholinyl, 4-thiomorpholinyl or 1-loweralkyl-4-piperazinyl.

A preferred roup of such compounds includes derivatives in which one or more of the hydrogens of the phenyl rings is replaced by substituents selected from the group consisting of hydrogen, an alkyl having up to 6 carbon atoms, an alkenyl group having up to 6 carbon atoms, a perfluoroalkyl group having up to 4 carbon atoms, a phenyl or a substituted phenyl radical, a dialkylamino group having up to 8 carbon atoms, an alkylsulfonylamino group having up to 4 carbon atoms, hydroxyl, and alkoxyl group having up to 4 carbon atoms, mercapto, an alkylmercapto group having up to 4 carbon atoms or a halogen such as fluoro or chloro.

An especially preferred group of compounds of the invention are represented by the following structural formula:

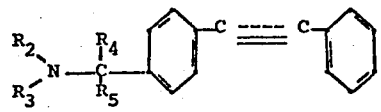

in which one or more of the hydrogens of the benzenoid rings may be replaced with fluoro, lower alkoxy of 1–4 carbons, preferably methoxy, lower alkyl of from 1–4 carbons, preferably methyl, hydroxy, alkyl mercapto, alkyl sulfonyl, and trifluoromethyl, wherein $R_2$ and $R_3$ are hydrogen and the same or different lower alkyl substituents of from 1 to 4 carbons and $R_4$ and $R_5$ are lower alkyl substituents of from 1 to 3 carbon atoms.

Illustrative of the compounds included within the scope of the invention are $\alpha,\alpha$-dimethyl-4-(phenylethynyl) benzylamine, N,$\alpha$,$\alpha$-trimethyl-4-(phenylethynyl)-benzylamine, N-methyl-cis or trans-$\alpha,\alpha$-dimethyl-4-styrylbenzylamine, 4-(phenylethynyl)benzylamine, 4-(4-methoxyphenylethynyl)-benzylamine, 4-(4-tolylethynyl)benzylamine, 4-(4-fluorophenylethynyl)benzylamine, trans-4-styryl benzylamine, trans-4-(4-methoxystyryl)benzylamine, the N-lower alkyl and the N,N-dilower alkyl especially the N-methyl and the N,N-dimethyl derivatives thereof.

The compounds represented above, in either their free base or salt form, possess useful pharmacological properties. In particular, they have been found to possess antiarrhythmic activity. It has been found that the administration of compounds of the present invention, depicted in the above formula, results in the prevention of arrhythmia in animals under conditions which ordinarily cause the development of arrhythmia in the animal 100% of the time.

It has further been found that administration of the compounds of the present invention will arrest an existing arrhythmia in the animal being treated and cause a resumption of normal cardiac rhythm. As antiarrhythmic agents, these compounds may be administered orally or parenterally. The formulations for administration may be prepared in conventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, fumaric acid, acetic acid, propionic acid, lactic acid, gluconic acid, maleic acid, succinic acid, tartaric acid and the like. Salts of these acids with the amine base are useful as the active component of the compositions in the method of this invention.

The daily doses are based on the total body weight of the test animal and vary between about 1.00 and 100.00 mg./kg. for mature animals. Thus, a unit dose based on four-times-a-day administration is between 2.5 mg. and 250 mg. for a 10 kg. dog, and a total daily dose for a 10 kg. dog would vary between about 10 mg. and 1,000 mg. For larger animals, up to 100 kg. and above, proportional dosages are employed, based on the weight of the animal. Suitable dosage units provided for the administration of the compositions used in the method of the invention are tablets, capsules (which may be suitably formulated for either immediate or sustained release), syrups, elixirs, parenteral solutions and the like. These dosage forms preferably contain per unit one or more multiples of the desired dosage unit in combination with the pharmaceutically acceptable diluent or carrier required for preparing the dosage unit.

The compounds of my invention are prepared by a process outlined by the following structural formulas:

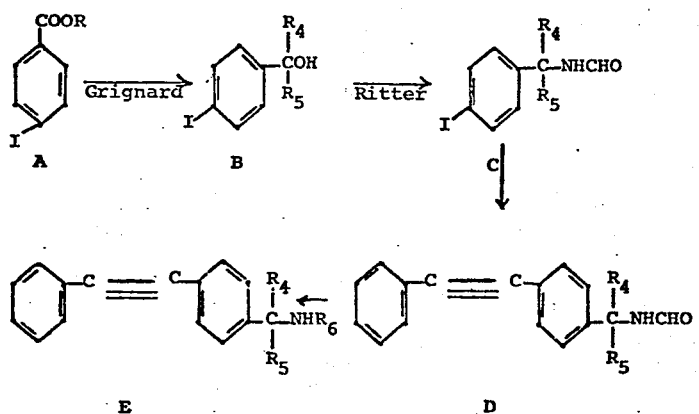

wherein R is lower alkyl; $R_4$ is lower alkyl of from 1–3 carbon atoms; $R_5$ is lower alkyl of from 1–3 carbon atoms; and $R_6$ is H or $CH_3$.

In accordance with the process of the invention a 4-iodobenzoic acid ester of formula A hereinabove is treated under anhydrous conditions with a lower alkyl Grignard reagent, for example, methyl magnesium bromide, and the product of the reaction hydrolyzed to produce an α,α-dialkyl-4-iodo benzyl alcohol in which the alkyl substituents are $C_1$–$C_3$ straight chain saturated aliphatic radicals, preferably methyl radicals.

In the instances in which $R_4$ and $R_5$ are different alkyl radicals, the starting material for the preparation of the tertiary alcohol is a 4-iodo-benzonitrile and the initial product obtained from the Grignard reaction and hydrolysis is a 4-iodophenylacetophenone. This ketone is then further reacted with an alkyl Grignard reagent followed by hydrolysis to produce the desired tertiary alcohol having $R_4$ and $R_5$ substituents which are different alkyl radicals.

This tertiary alcohol is then employed in a reaction which involves a reaction of a tertiary carbinol B under acid conditions. The starting material is mixed with hydrogen cyanide in sulfuric acid preferably generated by a mixture of sodium cyanide in a solution of sulfuric acid in acetic acid. The reaction was carried out for a period of from 15 minutes to approximately 24 hours, preferably for 6–10 hours, at 0°–50°C. When the compound α,α-dialkyl-4-iodo benzylalcohol is contacted with a mixture of sodium cyanide and sulfuric acid in acetic acid as the solvent for a period of 1 to 12 hours, the product obtained is the intermediate N-formyl-4-iodo-α,α-dialkyl benzylamine which is then mixed with an equimolar amount of a metal phenyl acetylide preferably cuprous phenyl acetylide of the formula:

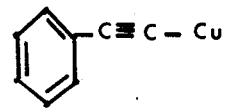

to form an N-formyl-α,α-dialkyl-4-(phenylethynyl)-benzylamine of the formula:

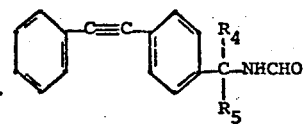

in which $R_4$ and $R_5$ are lower alkyl of from 1–3 carbons.

The product N-formyl-α,α-dialkyl-4-(4-phenylethynyl)benzylamine is then hydrolyzed by mixing with an aqueous solution of an organic or inorganic mineral acid or mixtures thereof. In the preferred instance an aqueous mixture of acetic and concentrated hydrochloric acid are employed and the reaction mixture is heated at the reflux temperature for about 2.5 hours. In practice the hydrolysis reaction takes place at from 30°–100°C. for a period of from 1–24 hours.

The corresponding N-lower alkyl, e.g. the n-methyl-α,α-dialkyl-4-(4-phenylethynyl9benzylamina. is produced by the reduction of the corresponding N-alkanoyl, e.g. the N-formyl-α,α-dialkyl-4-(4-phenylethynyl)-benzylamine, using an alkali metal or an alkali metal aluminum hydride to produce the resulting N-lower alkyl, e.g. the N-methyl-α,α-dialkyl-4-(4-phenylethynyl)benzylamine.

Preferably the reduction is carried out using lithium aluminum hydride as the reducing agent and in a benzene solution. Other inert organic solvents such as ethers. e.g. tetrahydrofuran, diethyl ether, or other solvents usually employed with lithium aluminum hydride may be used.

The temperature is not critical and room temperature, i.e. 25°C., is preferred but temperatures of from 0°–50° are satisfactory. The produced N-alkylbenzylamine is preferably extracted and isolated as the hydrochloride salt.

The primary amines produced in accordance with my invention are readily converted to the corresponding N-alkyl or N,N-dialkylamines employing well-known reactions as illustrated in the following reaction flow sheet.

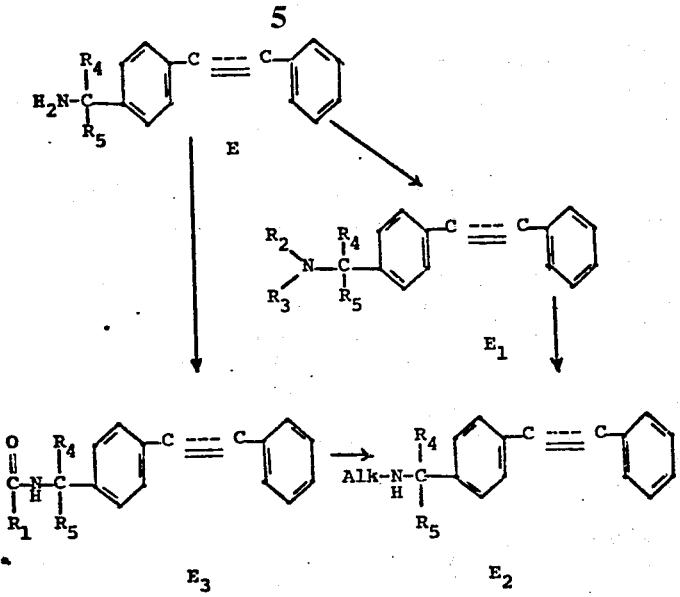

The corresponding N-(penylethenyl- or phenylethynylbenzyl) formamide $E_3$ in which $R_1$ is hydrogen is prepared by formylation of the benzylamine compound E employing conventional conditions and reagents such as formic acid or esters thereof for this purpose. The resulting formamide derivative can be recovered in conventional manner. The N,N-dimethylamine $E_1$, wherein $R_2$ and $R_3$ each represent methyl, is readily prepared by the treatment of the primary amine compound E with formaldehyde and formic acid in accordance with the known Eschweiler-Clarke modification of the Leuckart Reaction. Recovery of the N,N-dimethylamine is accomplished in conventional manner. The N-methylbenzylamine, represented by $E_2$ wherein Alk is methyl, may be prepared by either reduction of the corresponding N-(phenylethenyl- or phenylethynylbenzyl) formamide $E_3$ or by monodealkylation of the corresponding N,N-dimethylamine $E_1$ wherein $R_2$ and $R_3$ each represent methyl. Reduction of the formamido derivative is effected utilizing lithium aluminum hydride under the conditions set forth above. Similarly, dealkylation of the N,N-dimethylamine $E_1$ can be effected in known manner such as by treatment with cyanogen bromide followed by hydrolysis of the intermediate cyanamide or by treatment with a haloformate followed by hydrolysis of the resulting urethane intermediate. In each instance, the desired compound can be recovered employing conventional techniques.

The N-loweralkylamines and the N,N-diloweralkylamines corresponding to compounds $E_2$ and $E_3$, respectively, are likewise prepared from the corresponding primary amine E by analogous reactions. Thus, the primary amine E is treated with a lower aliphatic acid halide or anhydride of from 2–5 carbon atoms, e.g. acetyl chloride, acetic anhydride, propionyl chloride, butyryl chloride or valeryl chloride, to produce the N-alkanoyl amide corresponding to $E_3$ as, for example, the N-acetyl, N-propionyl, N-butyryl or N-valeryl amide. The thus-obtained amide is reduced to the corresponding N-loweralkyl benzylamine compound $E_2$ by reduction in the manner previously described, i.e. by reduction with lithium aluminum hydride. The secondary amine compounds $E_2$ produced in this manner are the N-loweralkyl derivatives of 4-(phenylethenyl or phenylethynyl)-α,α-dialkyl benzylamines as, for example, the N-ethyl, N-propyl, N-butyl and the N-amyl derivatives. The corresponding tertiary amines $E_1$, the N,N-diloweralkyl derivatives, are prepared from the secondary amines by repeating the process employed in the preparation of the secondary amines. Thus, the amides of the secondary amines are prepared and reduced with lithium aluminum hydride to produce the corresponding tertiary amines as, for example, the corresponding N,N-diethyl, N-ethyl-N-methyl, N,N-dipropyl, N,N-dibutyl and the N,N-diamyl derivatives of substituted and unsubstituted α,α-dialkyl phenylethenyl or phenylethynyl benzylamines.

In accordance with an alternative process for the preparation of the compounds of formula $E_1$, wherein

represents 1-pyrrolidinyl, 1piperidyl, 4-morpholinyl, 4-thiomorpholinyl or 1-loweralkyl-4-piperazinyl, the primary amine E is condensed with an α,ω-dihalo compound such as tetramethylene bromide, pentamethylene bromide, β,β'-dichlorodiethyl ether, β,β'-dichlorodiethyl sulfide, or an N-alkyl-β,β'-dichlorodiethyl amine.

In accordance with a further alternative process for the preparation of the primary, secondary and tertiary benzylamine products of my invention, a phenylethynyl or phenylethenyl halide of the formula shown below is converted by reaction with ammonia or an amine to produce the corresponding primary, secondary or tertiary amine as indicated below

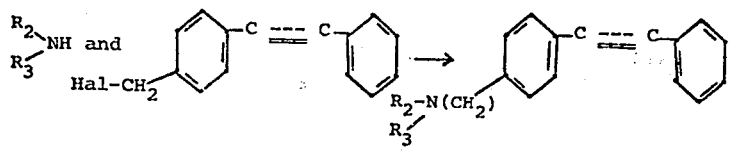

wherein Hal stands for halogen and $R_2$ and $R_3$ have the significance previously indicated. In this manner, there is produced in addition to the N-alkyl and N,N-dialkyl derivatives of the substituted and unsubstituted penylethenyl or phenylethynyl benzylamines or higher homologs thereof enumerated hereinabove, the corresponding compounds in which the amine nitrogen forms a part of a heterocyclic ring such as piperidyl, pyrrolidinyl, morpholinyl, thiomorpholinyl or 1-lower-alkyl-4-piperazinyl ring.

The starting compounds of the process of my invention, that is, the 4-iodo benzoic acid compounds and lower alkyl esters thereof, are either known compounds or may be readily prepared by simple procedures as for example by diazotization and replacement by iodine of the amino group in an appropriately substituted 4-amino benzoic acid.

The compounds of the invention which contain an ethenyl bridge can exist in two isomeric forms, the cis and trans isomers. These isomers have different physical characteristics and therefore are readily separable by conventional means as by crystallization.

Among the compounds prepared in accordance with the processes of the present invention are the $\alpha,\alpha$-dimethyl, $\alpha,\alpha$-diethyl, $\alpha,\alpha$-dipropyl, $\alpha$-methyl-$\alpha$-ethyl, $\alpha$-methyl-$\alpha$-propyl, $\alpha$-ethyl-$\alpha$-propyl, $\alpha$-methyl-$\alpha$-butyl benzylamines. The corresponding N-alkyl or N,N-dialkyl derivatives thereof, e.g. the N-methyl, N-ethyl, N-propyl, N,N-dimethyl, N,N-diethyl, N,N-dipropyl, N-methyl-N-ethyl, N-methyl-N-propyl, N-methyl-N-butyl and N-ethyl-N-propyl derivatives are prepared by methods described in the preceding pages for converting the benzylamine into the corresponding N-alkyl or N,N-dialkyl derivatives.

The corresponding ethylenic compounds, either cis or trans, of the formula

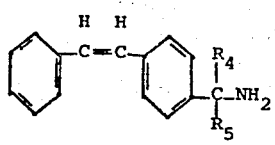

and the corresponding N-alkyl and the N,N-dialkyl derivatives wherein $R_4$ and $R_5$ are hydrogen or lower alkyl are produced by selective hydrogenation of the corresponding acetylenic compound of the formula

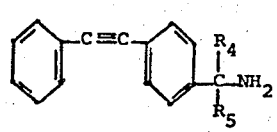

in the presence of a Lindlar type catalyst, i.e., palladium, deposited on barium sulfate and treated with quinoline.

The cis and trans isomers are ordinarily separable by crystallization and exhibit different bioactivity.

EXAMPLE 1

$\alpha,\alpha$-Dimethyl-4-(phenylethynyl)-benzylamine hydrochloride

A. Ethyl-4-iodobenzoate

A solution of 100 grams (0.403 mole) of p-iodobenzoic acid in 600 ml. of abs. ethanol containing 30 ml. of concentrated sulfuric acid is refluxed for 5 days. The cooled solution is poured over 350 grams of ice and is neutralized with saturated sodium carbonate solution. The oil that separates is extracted with six 150 ml. portions of ether. These ether extracts are combined, washed with water, dried over magnesium sulfate, and filtered. Evaporation of the ether gives 131.3 grams of ethyl-4-iodobenzoate as a chromatographically pure, clear, light oil.

B. $\alpha,\alpha$-Dimethyl-4-iodobenzyl alcohol

A solution of 2.76 grams of ethyl-4-iodobenzoate in 10 ml. of ether is placed in a dry flask. The solution is cooled in an ice bath and is stirred. Over a 5 minute period, 26.5 ml. of a 1.52 M ethereal solution of methyl magnesium bromide is added. The solution is stirred for 3 hours while in the ice bath. Water (6 ml.) is added dropwise while stirring. The solution is filtered and the filter cake is washed with six 20 ml. portions of ether. The combined ether phases are dried over magnesium sulfate and filtered. Removal of the ether gives $\alpha,\alpha$-dimethyl-4-iodobenzyl alcohol as a clear, light yellow liquid.

When the above experiment is repeated and ethyl-4-iodobenzoate is allowed to react with ethyl magnesium bromide or N-propyl magnesium bromide, the resulting compounds obtained are respectively $\alpha,\alpha$-diethyl-4-iodobenzyl alcohol or $\alpha,\alpha$-di(n-propyl)-4-iodobenzyl alcohol.

C. N-Formyl-$\alpha,\alpha$-dimethyl-4-iodobenzylamine

Into a flask is placed 19 ml. of glacial acetic acid. The flask is cooled in an ice bath and the acetic acid forms a slush. Pulverized sodium cyanide (4.18 grams) is added over a 30 minute period while stirring. A precooled solution of 10.3 ml. of concentrated sulfuric acid in 9.5 ml. of glacial acetic acid is added to the stirred cyanide mixture over 15 minutes. The ice bath is removed, and 19.92 grams of $\alpha,\alpha$-dimethyl-4-iodobenzyl alcohol is added over 10 minutes. The white suspension is stirred 90 minutes and is allowed to stand overnight at room temperature. The reaction mixture is poured over about 100 grams of ice, 100 ml. of water, and 100 ml. of ether. The mixture is neutralized with solid sodium carbonate. The aqueous phase is separated and extracted with two 100 ml. portions of ether. All of the ether phases are combined, washed three times with water, dried over magnesium sulfate, and filtered. Evaporation of the ether gives 18.17 grams of a reddish oil that crystallizes on standing. This solid is triturated with hot hexane and filtered to give N-formyl-$\alpha,\alpha$-dimethyl-4-iodobenzylamine as a light grey solid. The product may be recrystallized from a benzenecyclohexane mixture to give white needles, m.p. 121°–125°C.

When the preceding experiment is repeated but utilizing in place of $\alpha,\alpha$-dimethyl-4-iodobenzyl alcohol either $\alpha,\alpha$-diethyl-4-iodobenzyl alcohol or $\alpha,\alpha$-di(n-propyl)-4-iodobenzylalcohol there is obtained the corresponding N-formyl-$\alpha,\alpha$-diethyl-4-iodobenzylamine or N-formyl-$\alpha,\alpha$-di(n-propyl)-4-iodobenzylamine.

D. N-Formyl-α,α-dimethyl-4-(phenylethynyl)-benzylamine

A solution of 1.0 gram of N-formyl-α,α-dimethyl-4-iodobenzylamine in 14 ml. of pyridine is placed in a flask. The solution is stirred under a $N_2$ atmosphere. Cuprous phenylacetylide (0.57 gram) is added to this solution and the mixture is heated in an oil bath at 120°C. At first, the mixture is a yellow suspension, but within 1.5 hours, a homogenous dark amber solution is obtained. The reaction is heated for 10 hours at 120°C. The cooled reaction mixture is poured onto 150 ml. of water and extracted with three 75 ml. portions of a 1:1 ether-benzene mixture. The extracts are combined, washed with two 50 ml. portions of dilute hydrochloric acid, two 50 ml. portions of 5% sodium hydroxide, two 100 ml. portions of water, and dried over magnesium sulfate. After filtration and evaporation of the solvent, there remains 0.78 gram of N-formyl-α,α-dimethyl-4-(phenylethynyl)-benzylamine as a clear oil that crystallizes on standing. The product may be recrystallized from isopropanol, m.p. 135°–141° C.

The experiment is repeated using in place of N-formyl-α,α-dimethyl-4-iodobenzylamine the corresponding N-formyl-α,α-diethyl-4-iodobenzylamine or N-formyl-α,α-di(n-propyl)-4-iodobenzylamine with resultant production of N-formyl-α,α-diethyl-4-(phenylethynyl)-benzylamine or N-formyl-α,α-di(n-propyl)-4-(phenylethynyl)-benzylamine. E. α,α-Dimethyl-4-(phenylethynyl)-benzylamine hydrochloride A mixture of 0.50 gram of N-formyl-α,α-dimethyl-4-(phenylethynyl)-benzylamine, 10.7 ml. of glacial acetic acid, 6.7 ml. of water, and 1.07 ml. of concentrated hydrochloric acid is stirred and refluxed for 2.5 hours. The solution is evaporated to dryness and α,α-dimethyl-4-(phenylethynyl)-benzylamine hydrochloride is obtained as a light tan solid. The product is recrystallized from an isopropyl alcohol-methanol-ether mixture to give pure α,α-dimethyl-4-(phenylethynyl)-benzylamine hydrochloride, m.p. 275°–278° (decomp.).

Anal. Calcd. for $C_{17}H_{18}N$ Cl: C, 75.13; H, 6.68; N, 5.15; Cl, 13.04. Found: C, 74.18; H, 6.77; N, 5.30; Cl, 13.11.

When the preceding experiment is repeated using in place of N-formyl-α,α-dimethyl-4-(phenylethynyl)-benzylamine the corresponding N-formyl-α,α-diethyl-4-(phenylethynyl)-benzylamine or N-formyl-α,α-di(n-propyl)-4-(phenylethynyl)-benzylamine there is obtained respectively α,α-diethyl-4-(phenylethynyl)-benzylamine and α,α-di(n-propyl)-4-(phenylethynyl)-benzylamine.

EXAMPLE 2

N,α,α-Trimethyl-4-(phenylethynyl)-benzylamine hydrochloride

A solution of 2.92 grams of N-formyl-α,α-dimethyl-4-(phenylethynyl)-benzylamine in 30 ml. of benzene is placed in a dry flask. The solution is stirred. A solution of 6.6 grams of a 70% "Red-Al" solution in benzene is diluted with 30 ml. of benzene; this solution is added dropwise over approximately 30 minutes to the solution of N-formyl-α,α-dimethyl-4-(phenylethynyl)-benzylamine. The reaction is hydrolyzed with water and is extracted thoroughly with a 1:1 benzene-ether solvent mixture. The combined extracts are dried over magnesium sulfate, filtered, and the solvent is evaporated to give 3.34 gm. of an oil. This oil is dissolved in ether and treated with ethanolic hydrogen chloride. The precipitate is collected and recrystallized from isopropanol to give N,α,α-trimethyl-4-(phenylethynyl)-benzylamine hydrochloride, m.p. 266°–268° C.

Anal. Calcd. for $C_{18}H_{19}N.HCl$: C, 75.64; H, 7.05; N, 4.90. Found: C, 75.72; H, 6.90; N, 4.76.

When the above experiment is repeated using as alternate starting materials either N-formyl-α,α-diethyl-4-(phenylethynyl)-benzylamine or N-formyl-α,α-di(n-propyl)-4-(phenylethynyl)-benzylamine there is obtained respectively α,α-diethyl-N-methyl-4-(phenylethynyl)-benzylamine or N-methyl-α,α-di(n-propyl)-4-phenylethynyl benzylamine.

EXAMPLE 3

When Example 1 is repeated utilizing the starting materials indicated the respective indicated products are obtained:

| Starting Carbinol | | | Cuprous Phenylacetylide | Product Amine | | |
|---|---|---|---|---|---|---|
| $R_4$ & $R_5$ | X | X' | | $R_4$ & $R_5$ | X | X' |
| methyl | hydrogen | 3-fluoro | | methyl | hydrogen | 3-fluoro |
| " | " | 4-fluoro | | " | " | 4-fluoro |
| " | " | 2-methoxy | | " | " | 2-methoxy |
| " | " | 3-ethoxy | | " | " | 3-ethoxy |
| " | " | 4-methoxy | | " | " | 4-methoxy |
| " | " | 2-methyl | | " | " | 2-methyl |
| " | " | 3-methyl | | " | " | 3-methyl |
| " | " | 4-methyl | | " | " | 4-methyl |
| " | " | 4-ethyl | | " | " | 4-ethyl |
| " | " | 2-hydroxy | | " | " | 2-hydroxy |
| " | " | 3-hydroxy | | " | " | 3-hydroxy |
| " | " | 4-hydroxy | | " | " | 4-hydroxy |
| ethyl | " | 3-fluoro | | ethyl | " | 3-fluoro |
| " | " | 4-fluoro | | " | " | 4-fluoro |
| " | " | 2-methoxy | | " | " | 2-methoxy |
| " | " | 3-ethoxy | | " | " | 3-ethoxy |
| " | " | 4-methoxy | | " | " | 4-methoxy |
| " | " | 2-methyl | | " | " | 2-methyl |
| " | " | 3-methyl | | " | " | 3-methyl |
| " | " | 4-methyl | | " | " | 4-methyl |
| " | " | 4-ethyl | | " | " | 4-ethyl |

-continued

| Starting Carbinol | | Cuprous Phenylacetylide | Product Amine | | |
|---|---|---|---|---|---|
| $R_4$ & $R_5$ | X | X' | $R_4$ & $R_5$ | X | X' |
| " | " | 2-hydroxy | " | " | 2-hydroxy |
| " | " | 3-hydroxy | " | " | 3-hydroxy |
| " | " | 4-hydroxy | " | " | 4-hydroxy |
| methyl | 3-fluoro | hydrogen | methyl | 3-fluoro | hydrogen |
| " | 4-fluoro | " | " | 4-fluoro | " |
| " | 2-methoxy | " | " | 2-methoxy | " |
| " | 3-ethoxy | " | " | 3-ethoxy | " |
| " | 4-methoxy | " | " | 4-methoxy | " |
| " | 2-methyl | " | " | 2-methyl | " |
| " | 3-methyl | " | " | 3-methyl | " |
| " | 4-methyl | " | " | 4-methyl | " |
| " | 4-ethyl | " | " | 4-ethyl | " |
| " | 2-hydroxy | " | " | 2-hydroxy | " |
| " | 3-hydroxy | " | " | 3-hydroxy | " |
| " | 4-hydroxy | " | "4-hydroxy | " | " |
| " | hydrogen | 4-methyl-sulfonyl | " | hydrogen | 4-methyl-sulfonyl |
| " | " | 4-methyl mercapto | " | " | 4-methyl mercapto |
| " | " | 4-trifluoro-methyl | " | " | 4-trifluoro-methyl |

EXAMPLE 4

4-(Phenylethynyl)-benzyl chloride

Thionyl chloride, 7 ml., is added dropwise to a stirred solution of 6.0 g. (0.0288 mole) of 4-(phenylethynyl) benzyl alcohol in 100 ml. of dry chloroform at room temperature and the mixture is stirred for 6 hours. Solvent is evaporated under reduced pressure and at a temperature below 50°. The residue is freed from traces of thionyl chloride by dissolution in dry benzene and evaporation under reduced pressure. This process is repeated and the residual solid product is purified by sublimation in vacuo; m.p. 61.5°–63.5°C.

Anal. Calc'd. for $C_{15}H_{11}Cl$: C, 79.47; H, 4.89. Found: C, 79.60, 79.48; H, 4.98, 4.95.

EXAMPLE 5

N-(4-phenylethynylbenzyl)-piperidine 4-(Phenylethynyl)-benzyl chloride, 0.57 g. (2.5 mmole), is added to 5 ml. of piperidine and the mixture, from which a precipitate separates, is stirred for about 3 hours at room temperature. After evaporation of the bulk of the excess piperidine under reduced pressure, the residue is triturated with benzene and the insoluble piperidine hydrochloride removed by filtration. The benzene filtrate is washed with water and dried ($MgSO_4$). Evaporation of the benzene under reduced pressure leaves 0.74 g. of the product as the residual oil. This oil is dissolved in isopropyl alcohol and treated with a slight excess of 7.2 N. hydrogen chloride in absolute ethanol. The white crystalline precipitate is collected after chilling the mixture and is recrystallized from isopropyl alcohol to give 0.662 g. of N-(4-phenylethynylbenzyl)-piperidine hydrochloride, m.p. 254°–256°C.

Anal. Calc'd. for $C_{20}H_{21}N.HCl$: C, 77.03; H, 7.11; N, 4.49. Found: C, 77.25; H, 7.21; N, 4.65.

EXAMPLE 6

N-Cyclopropyl-4-(phenylethynyl)-benzylamine

A solution of 0.9 g. (4 mmole) of 4-(phenylethynyl)-benzyl chloride in 3 ml. of cyclopropylamine is heated to refluxing for 2 hours and then is allowed to stand at room temperature for several days. Another 1 ml. of cyclopropylamine is added and the solution is heated to refluxing for 4 hours. After evaporation of the excess cyclopropylamine, the residue is triturated with ether and the precipitate removed by filtration. The ethereal filtrate is evaporated and the residual oil dissolved in benzene. This solution is shaken with 10 ml. of 3N hydrochloric acid. The white crystalline hydrochloride salt of the product precipitates. It is collected and recrystallized twice from absolute methanol to give N-cyclopropyl-4-(phenylethynyl)-benzylamine hydrochloride, m.p. 210°–212°C. dec.

Anal. Calc'd. for $C_{18}H_{17}N.HCl$: C, 76.17; H, 6.39; N, 4.93. Found: C, 76.35; H, 6.29; N. 4.95.

What is claimed is:

1. A compound of the formula

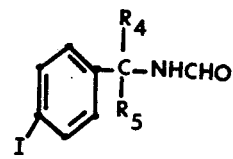

wherein $R_4$ and $R_5$ are lower alkyl substituents.

2. N-formyl-α,α-dimethyl-4-iodobenzylamine according to claim 1.

3. A compound of the formula wherein $R_4$ and $R_5$ are lower alkyl substituents.
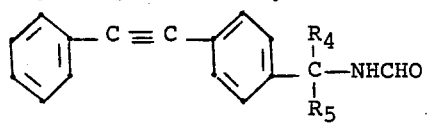
4. N-formyl-α,α-dimethyl-4-(phenylethynyl)-benzylamine.
5. 4-(Phenylethynyl)-benzyl chloride.
* * * * *

UNITED STATES PATENT AND TRADEMARK OFFICE
CERTIFICATE OF CORRECTION

PATENT NO. : 3,957,871
DATED : May 18, 1976
INVENTOR(S) : David C. Remy

It is certified that error appears in the above-identified patent and that said Letters Patent are hereby corrected as shown below:

In Column 13, lines 1-5, "wherein $R_4$ and $R_5$ are lower alkyl substituents.

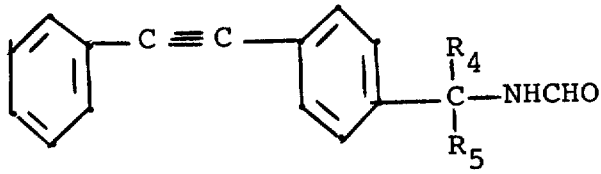

"

should read

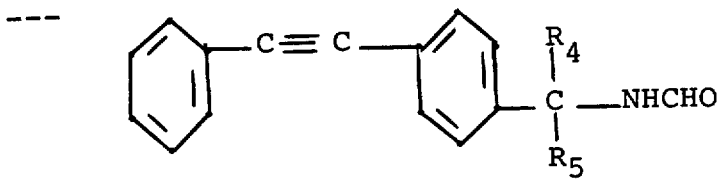

wherein $R_4$ and $R_5$ are lower alkyl substituents.---

Signed and Sealed this

Third Day of August 1976

[SEAL]

Attest:

RUTH C. MASON
Attesting Officer

C. MARSHALL DANN
Commissioner of Patents and Trademarks